United States Patent [19]

Hyatt et al.

[11] 4,328,162

[45] May 4, 1982

[54] PROCESS FOR PREPARING 9,11-UNSATURATED STEROIDAL COMPOUND FROM THE CORRESPONDING SATURATED STEROIDAL COMPOUND

[75] Inventors: John A. Hyatt; Charles A. McCombs, both of Kingsport, Tenn.

[73] Assignee: Eastman Kodak Company, Rochester, N.Y.

[21] Appl. No.: 184,552

[22] Filed: Sep. 5, 1980

[51] Int. Cl.$^3$ .............................................. C07J 5/00
[52] U.S. Cl. .............................. 260/397.45; 260/397.2
[58] Field of Search ...... 260/397.5, 397.45, 239.55 D, 260/397.43

[56] References Cited

U.S. PATENT DOCUMENTS 4,061,661  12/1977  Kerb et al. .................... 260/397.45
4,252,719  2/1981   Breslow et al. ............ 260/239.55 D

OTHER PUBLICATIONS

Breslow et al. "Journal of American Chem. Soc." (1977), vol. 99, No. 3, pp. 905–915.

*Primary Examiner*—Elbert L. Roberts

*Attorney, Agent, or Firm*—Clyde L. Tootle; Daniel B. Reece, III

[57] ABSTRACT

The present invention provides a non-fermentation process for placing unsaturation at the 9,11 position in a steroidal compound. Also, the present invention provides a process whereby the modified steroidal compound can be separated from the reaction mixture without the use of chromatography. More specifically, the present invention provides a process whereby a steroid compound such as 17-α-hydroxy-progesterone is reacted to form the meta iodoaryl benzoate. The iodoarylbenzoate is then irradiated with visible light in the presence of an alkyl-m-iodobenzoate dichloride to form the 9α-chloro steroid derivative. The chlorinated steroid derivative can then be hydrolized to provide a 9α-chloro steroidal alcohol and m-iodobenzoic acid. The m-iodobenzoic acid is extracted by the use of an aqueous base. The chlorinated steroidal alcohol can then be recovered and converted by conventional dehalogenation techniques to steroidal unsaturated compound having a double bond in the 9,11 position of the steroid nucleus. Alternatively, the chlorinated steroid derivative can be dehalogenation and then hydrolized.

9 Claims, No Drawings

PROCESS FOR PREPARING 9,11-UNSATURATED STEROIDAL COMPOUND FROM THE CORRESPONDING SATURATED STEROIDAL COMPOUND

The present invention provides a non-fermentation process for placing unsaturation at the 9,11 position in a steroidal compound. Also, the present invention provides a process whereby the modified steroidal compound can be separated from the reaction mixture without the use of chromatography. More specifically, the present invention provides a process whereby a steroid compound such as 17-α-hydroxyprogesterone is reacted to form the meta-iodoaryl benzoate steroid. The iodoaryl benzoate is then irradiated with visible light in the presence of an alkyl-m-iodobenzoate to form the 9α-chloro steroid derivative. The chlorinated steroid derivative can then be hydrolized to provide a 9α-chloro steroidal alcohol and m-iodobenzoic acid. The m-iodobenzoic acid is extracted by the use of an aqueous base. The chlorinated steroidal alcohol can then be recovered and converted by conventionl dehalogenation techniques to steroidal unsaturated compound having a double bond in the 9,11 position of the steroid nucleus. Alternatively, the chlorinated steroid derivative can be dehalogenated and then hydrolized.

It is known in the art to selectively chlorinate a particular position on a steroid by the use of an attached iodobenzoate template or directing group with iodobenzene dichloride as the chlorine source as shown by Breslow [J. Am. Chem. Soc. 99, 905 (1977)] and Kerb (U.S. Pat. No. 4,061,661 to Schering A.G.) This method of selectively introducing chlorine, and subsequently unsaturation, into the steroid molecule is of considerable value in the preparation of pharmaceutically important steroids, such as the cortisteroid family. This prior art has certain disadvantages such as the necessity of separation of both iodobenzene and m-iodobenzoic acid from the steroid product, which generally requires chromatography. Therefore, it would be an improvement and an advance in the state of the art to provide a process whereby steroids can be selectively chlorinated and the resultant chlorinated product can be separated from the iodoaryl by-products in an easy recovery method that avoids the necessity for chromatographic separations.

In accordance with the present invention, steroidal compounds are selectively chlorinated and subsequently dehalogenated providing unsaturated steroidal compounds. The unsaturated steroidal compounds are prepared from the corresponding saturated compounds by reacting a hydroxyl group in position 3α or 17α of the saturated steroid compound with a derivative of meta-iodobenzoic acid derivative to form a 3α- or 17α-m-iodobenzoate ester. This substituted sterol ester iodine is then irradiated for 1 to 20 minutes with visible or ultraviolet light in the presence of an alkyl-m-iodobenzoate dichloride to form a 9α-chloro steroidal compound. For example, in one embodiment, a 3α-hydroxy steroidal compound can be reacted with m-iodobenzoyl chloride. The resultant 3α-steroidal ester such as 3α-cholestanyl-m-iodobenzoate is then irradiated in the presence of an alkyl-m-iodobenzoate dichloride, as for example, methyl-m-iodobenzoate dichloride, to provide a 9α-chlorocholestanyl-3α-m-iodobenzoate. In another embodiment, a 17α-hydroxysteroid can be reacted with m-iodobenzoyl chloride to provide a 17α-m-iodobenzoyloxy steroid which when irradiated in the presence of an alkyl m-iodobenzoate dichloride provides a 9α-chloro steroid ester. The solvent is then removed from the irradiation reaction mixtue as, for example, by evaporation. The mixture, consisting of the above-mentioned 9α-chlorosteroid-m-iodobenzoate ester and alkyl-m-iodobenzoate, can then be refluxed with aqueous caustic for a period of 10 minutes to 1 hour. The 9α-chlorosteroid alcohol can be recovered by filtration or solvent extractions, and m-iodobenzoic acid is recovered by acidification of the basic aqueous residue. Therefore, the use of alkyl-m-iodobenzoate dichloride instead of iodobenzene dichloride previously taught by Breslow and Kerb renders the recovery of steroid products easier by virtue of not generating iodobenzene as a by-product, and by allowing easy recovery of both the chlorine source and template, or directing group, as m-iodobenzoic acid. Alternately, the 17α-hydroxyprogesterone can be reacted with m-iodobenzoyl chloride to form the steroidal 17α-m-iodobenzoate. This ester is then irradiated in the presence of methyl-m-iodobenzoate dichloride in methylene chloride solution to form the 9α-chloro compound and further processed as described herein before.

The reaction of the saturated steroid alcohol with meta-iodobenzoic acid derivative is carried out with a strong base and is preferably carried out in a suitable solvent. The base activates the hydroxyl group so that the iodobenzoic acid derivatives can easily react to form the ester linkage. Bases which are useful are, for example, sodium hydride, sodium methoxide, sodium ethoxide, potassium tert-butoxide, n-butyl lithium, methyl lithium, phenyl lithium, methyl magnesium bromide and 4-dimethylamine pyridine and the like. Suitable solvents are, for example, hydrocarbon solvents such as hexane, benzene, toluene and the like; ether solvents such as diethyl ether, tetrahydrofuran, dioxane, glyme, diglyme and the like; amines such as pyridine, dimethylforamide, N-methylpyrridone, as well as nitriles such as acetonitrile. The amount of solvent used can vary in amounts but generally is that amount required to dissolve the reactants. The temperature can vary but generally is between $-20°$ C. to about $80°$ C. The time required for the reaction can be from about ten minutes to several hours depending on the temperature and amount of solvent used. The metaiodobenzoic acid derivatives can be the acid halides such as meta-iodobenzyl chloride, meta-iodobenzyl, chloride, meta-iodobenzyl bromide or meta-iodobenzyliodide as well as meta-iodobenzyl imidazolide.

The steroid-m-iodobenzoate ester is then isolated and chlorinated. The chlorination is carried out in the presence of a lower alkyl-m-iodobenzoate dichloride in a suitable solvent. The alkyl-m-iodobenzoate dichloride can be methyl-m-iodobenzoate dichloride or other lower alkyl-m-iodobenzoate dichlorides such as the ethyl, proyl, butyl, pentyl-m-iodobenzoate dichlorides and the like.

Suitable solvents for the chlorination are, for example, carbontetrachloride, dichloroethane, trichlorobenzene, tetrachloroethane, benzene and the like.

The amount of solvent and temperature are the same as used in the preparation of the meta-iodoaryl benzoate steroid. The chlorination can be carried out using an irradiation source or if desired a peroxide can be used such as, for example, benzoyl peroxide. Irrodiation sources useful are, for example, any ultraviolet light source such as, for example, commercially available sunlamps. The solvent is then removed from the irradiated reaction mixture. The 9α-chlorosteroid-m-iodobenzoate can then be dehydrohalogenated to provide unsaturation and then be refluxed in aqueous alkali to split off the ester linkage by an alkaline saponification or the saponification can be carried out prior to dehydrohalogenation.

The chlorinated steroidal compounds can be dehydrohalogenated by treating in the homogeneous phase with a dehydrohalogenating silver salt, e.g., silver perchlorate, nitrate, acetate, oxide or other suitable silver salt soluble in the reaction solvent, whereupon the 9α-chlorine atom is split off as the insoluble silver chloride and is precipitated, with the formation of the 9,11-double bond. Solvents which permit operation in a homogeneous phase are those in which the silver salt is soluble, such as, for example, acetone, acetic acid and lower alcohols or water, and/or mixtures of such organics and water in an amount of 10 to 90% water. The amount of solvent, temperature and time are the same as set forth hereinbefore.

The chlorinated steroidal compound can also as noted above in an alternative process first be treated with aqueous alkali to split off the ester linkage by an alkaline saponification such as by the use of a methanolic potassium hydroxide solution.

The invention can be further illustrated by the following examples, although it will be understood that these examples are included merely for purpose of illustration and are not intended to limit the scope of the invention unless otherwise specifically indicated.

EXAMPLE 1

Preparation of Methyl-m-Iodobenzoate Dichloride

A solution of 5.0 g methyl-m-iodobenzoate in 70 ml chloroform was cooled to 0°–10° and treated with gaseous chlorine for 1 hour. The resulting yellow solution was evaporated to afford 6.2 g methyl-m-iodobenzoate dichloride as yellow needles, mp=108°–110°. IR: 5.83, 7.80, 8.00, 8.90, 9.18, 10.52, 11.12, 12.39, and 13.48.

EXAMPLE 2

Preparation of 3α-Cholestany-m-Iodobenzoate (a) From 3α-cholestanol: A solution of 3.89 g of 3α-cholestanol in 20 ml of pyridine was treated with 2.66 g of m-iodobenzoyl chloride at 0° and let warm to 22° over 14 hrs. The reaction mixture was then poured into 3000 ml ice water and the precipitated 3α-cholestanyl-m-iodobenzoate recovered by filtration. Recrystallization from ethanol provided a product having a m.p. of 85°–87° C.

(b) From 3β-cholestanol: The procedure of Breslow et al (J. Am. Chem. Soc. 99, 912 (1978) was also used to prepare 3α-cholestanyl-m-iodobenzoate. A solution of 17.34 g (of 3β-cholestanol, 10.0 g of m-iodobenzoic acid, and 11.7 g of triphenyl phosphine in 500 ml of dry tetrahydrofuran was treated at 25° with a solution of 7.76 g diethylazodicarboxylate in >0 ml of tetrahydrofuran. After stirring at 25° for 18 hrs., the solvent was removed in vacuo to give a gummy residue. The gum was treated with a solution of acetone (5:1) in hexane, which caused precipation of by-product triphenylphosphine oxide, which was collected by filtration and discarded. The filtrate was again stripped of solvent in vacuo and the residue crystallized from ethanol to give 21.5 g (78.1 yield) of 3α-cholestanyl-m-iodobenzoate, mp 85.7°.

EXAMPLE 3

Use of Methyl-m-iodobenzoate Dichloride in a Selective Steroid Halogenation

A solution of 1.0 g of 3α-cholestanyl-m-iodobenzoate and 0.62 g methyl-m-iodobenzoate dichloride in 100 ml dichloromethane was purged with argon, cooled to 5°–15°, and irradiated with a 275-watt sunlamp held 6" from the reaction vessel for 6.0 minutes, at which time TLC analysis disclosed complete consumption of 3α-cholestanyl-m-iodobenzoate and formation of the corresponding 9α-chloro compound along with methyl-m-iodobenzoate. The solvent was removed by evaporation and the crude mixture of 9α-chloro compound and methyl-m-iodobenzoate was treated with 10 ml of p-dioxane, 10 ml of 10% potassium hydroxide in methanol, and refluxed for about 0.5 hour. The mixture was then poured into 250 ml ice water and the $9,11$-cholesten-3α-ol recovered by filtration. After recrystallization from methanol, 0.58 g (92%), $9,11$-cholesten-3α-ol of greater than 90% purity (as judged by NMR and chromatographic analysis) was obtained. Properties of $9,11$-cholesten-3α-ol were in accord with those previously reported in the literature.

The filtrate from $9,11$-cholesten-3α-ol was rendered acidic and the m-iodobenzoic acid thereby precipitated and was filtered off. The yield of recovered acid was 0.81 g (95%).

EXAMPLE 4

Preparation of 17α-(m-Iodobenzoyloxy)Progesterone

A solution of 15 g (0.0455 mole) 17α-hydroxyprogesterone in 250 ml dry tetrahydrofuran was cooled to 5°–10° and treated with 32.7 ml of 1.6 M n-butyllithium in hexane. After 0.5 hr. a solution of 13.9 g of m-iodobenzoyl chloride in 15 ml dry tetrahydrofuran was added, the mixture was stirred at reflux for one hour. The mixture was then cooled, poured into 1.5 l ice water, and extracted with ether. The crude ether extracted product after removal of the ether was purified to afford 11.6 g 17α-(m-iodobenzoyloxy)progesterone as a foam. A sample was crystallized from ethanol and had mp. 172°–178°; mass spectrum showed m/e 560.

Analysis: Calc'd, C, 60.00; H, 5.93; Found, C, 59.88, H, 5.94.

EXAMPLE 5

Preparation of 9α-Chloro-17α(m-iodobenzoyloxy) Progesterone

A solution of 0.28 g of 17α-(m-iodobenzoyloxy)-progesterone in 50 ml dichloromethane was treated with 0.26 g methyl-m-iodobenzoate dichloride, cooled to 5°–10°, and purged with argon for 15 min. The mixture was then irradiated with a 275-watt sunlamp from a distance of 6" for 20 min. TLC analysis of the mixture disclosed the presence of one major product, 9α-chloro-17α-(m-iodobenzoyloxy)progesterone, and traces of starting material 17α-(m-iodobenzoyloxy)progesterone and an unidentified by-product. Methyl-m-iodobenzoate was also present. A sample of pure 9α-chloro-17α-(m-iodobenzoyloxy)progesterone was obtained by preparative TLC, and had IR and NMR spectra in accord with the proposed structure.

EXAMPLE 6

Preparation of 17α-(m-Iodobenzoyloxy)pregna-4,9(11)diene-3,20-dione

A crude photolysis mixture containing 9α-chloro-17α-(m-iodobenzoyloxy)progesterone (as described in Example 5) was subjected to chromatography on Merck (Darmstadt) #7734 Silica Gel, using 1% methanol/chloroform elution. The chloro compound 9α-chloro-17α-(m-iodobenzoyloxy)progesterone underwent dehydrochlorination on the column, and 17α-(m-iodobenzoyloxy)pregna-4,9(11)diene-3,20-dione was obtained by continued elution. 9α-Chloro-17α-(m-iodobenzoyloxy)progesterone showed m/e 558 in the mass spectrum, and the proton on $C_{11}$ was seen at 4.98 in the NMR spectrum.

EXAMPLE 7

Preparation of 9α-Chloro-17α-hydroxyprogesterone

A solution of 20 mg. 9α-chloro-17α-(m-iodobenzoyloxy)-progesterone (contaminated with methyl-m-iodobenzoate, as per Example 5) in 3 ml methanol was treated with about 0.4 ml 10% aq. NaOH and refluxed 15 min. The mixture was diluted to 20 ml with water and extracted with dichloromethane. Evaporation of the extract provided 9α-chloro-17α-hydroxyprogesterone as a foam; the mass spectrum showed m/e 328 (M-HCl), 310 (M-HCl, -$H_2O$), and 37 (HCl). Acification of the aqueous residue from the extraction gave m-iodobenzoic acid.

EXAMPLE 8

Preparation of 17α-Hydroxypregna-4,9(11)diene-3,30-dione (a) From 9α-chloro-17α-hydroxyprogesterone: A solution of 0.67 g crude 9α-chloro-17α-hydroxyprogesterone in 25 ml acetone was treated with 0.5 ml 25% aq. $AgNO_3$ and let stand at 25° for 8 hrs. The reaction mix was filtered and evaporated to afford crude 17α-hydroxypregna-4,9(11)diene-3,20-dione. An analytical sample of 17α-hydroxypregna-4,9(11)diene-3,20-dione was secured by thin layer chromotography (TLC) and had IR, $^1H$ NMR, $^-C$ NMR, and mass spectra in accord with the proposed structure.

(b) The hydrolysis of 17α-(m-iodobenzoyloxy)pregna-4,9(11)diene-3,20-dione was carried out similarly to that described in Example 6 above. The product was identical to that of Example 8a.

The present invention provides a chemical method for placing unsaturation at the 9,11 positions in a steroidal compound. Such unsaturated steroidal compounds, such as 17α-hydroxypregna-4,9(11)diene-3,20 dione, are useful as an antiarthritic drug and also as a corticosteroid intermediate.

The invention has been described in detail with particular reference to preferred embodiments thereof, but it will be understood that variations and modifications can be effected within the spirit and scope of the invention.

We claim:

1. Process for preparing 9,11-unsaturated steroidal compounds from the corresponding saturated 3α- or 17α-hydroxy steroidal compounds which comprises reacting the hydroxyl group of said saturated steroidal compound with a meta-iodobenzoic acid derivative to form a 3α- or 17α-m-iodobenzoate ester, irradiating said 3α- or 17α-m-iodobenzoate ester in the presence of an alkyl-m-iodobenzoate dichloride to form the corresponding 9α-chloro steroid ester, and dehydrochlorinating said 9α-chlorosteroid ester to prepare the 9,11 unsaturated steroidal compound.

2. A process according to claim 1 wherein said saturated 3α-steroidal compound is 3α-cholestanol.

3. A process according to claim 2 wherein said meta-iodobenzoic acid derivative is m-iodobenzyl chloride.

4. A process according to claim 3 wherein said alkyl-m-iodobenzoate dichloride is methyl-m-iodobenzoate.

5. A process according to claim 4 comprising the further step of saponifying said 9,11 unsaturated steroidal compound to provide the 3α-hydroxy-9,11-unsaturated steroidal compound.

6. A process according to claim 1 wherein said saturated 17α-steroidal compound is 17α-hydroxyprogesterone.

7. A process according to claim 6 wherein said meta-iodobenzoic acid derivative is m-iodobenzoyl chloride.

8. A process according to claim 7 wherein said alkyl-m-iodobenzoate dichloride is methyl-m-iodobenzoate.

9. A process according to claim 8 comprising the further step of saponifying said 9,11-unsaturated steroidal compound to provide the 17α-hydroxy-9,11-unsaturated steroidal compound.

* * * * *